United States Patent
Fukuyama et al.

(10) Patent No.: US 12,067,703 B2
(45) Date of Patent: Aug. 20, 2024

(54) GRAIN SIZE ESTIMATION DEVICE, GRAIN SIZE ESTIMATION METHOD, GRAIN SIZE ESTIMATION PROGRAM, AND GRAIN SIZE ESTIMATION SYSTEM

(71) Applicants: Kabushiki Kaisha Toshiba, Minato-ku (JP); Toshiba Digital Solutions Corporation, Kawasaki (JP)

(72) Inventors: Kota Fukuyama, Fuchu (JP); Hisanori Hata, Kawasaki (JP); Takayuki Ikeya, Fuchu (JP)

(73) Assignees: Kabushiki Kaisha Toshiba, Tokyo (JP); Toshiba Digital Solutions Corporation, Kawasaki (JP)

( * ) Notice: Subject to any disclaimer, the term of this patent is extended or adjusted under 35 U.S.C. 154(b) by 466 days.

(21) Appl. No.: 17/441,473

(22) PCT Filed: Sep. 18, 2020

(86) PCT No.: PCT/JP2020/035524
§ 371 (c)(1),
(2) Date: Sep. 21, 2021

(87) PCT Pub. No.: WO2022/059186
PCT Pub. Date: Mar. 24, 2022

(65) Prior Publication Data
US 2022/0318983 A1    Oct. 6, 2022

(51) Int. Cl.
*G06T 7/00* (2017.01)
*G01N 33/204* (2019.01)
*G06T 7/60* (2017.01)

(52) U.S. Cl.
CPC ......... *G06T 7/0004* (2013.01); *G01N 33/204* (2019.01); *G06T 7/60* (2013.01);
(Continued)

(58) Field of Classification Search
CPC ... G01N 2291/0234; G01N 2291/0289; G01N 33/204; G06T 7/0004; G06T 7/60;
(Continued)

(56) References Cited

U.S. PATENT DOCUMENTS

| | | | |
|---|---|---|---|
| 2015/0178415 A1 | 6/2015 | Sano et al. | |
| 2015/0199617 A1* | 7/2015 | Kuwajima | G06N 20/00 706/20 |

(Continued)

FOREIGN PATENT DOCUMENTS

| | | | |
|---|---|---|---|
| CN | 103913416 A | 7/2014 | |
| CN | 109034217 A * | 12/2018 | ........... G06K 9/6256 |

(Continued)

OTHER PUBLICATIONS

Peregrina-Barreto et al., "Automatic grain size determination in microstructures using image processing" (Year: 2012).*

(Continued)

*Primary Examiner* — Dung Hong
(74) *Attorney, Agent, or Firm* — Maier & Maier, PLLC

(57) ABSTRACT

According to one embodiment, a grain size estimation device includes an acquisition unit that acquires a captured image of a surface segment of an object inducing metal; and an estimation unit that estimates a grain size of the surface segment of the object indicated in the acquired image, based on a predictive model generated by machine learning using images of metal surfaces and grain sizes in the metal surfaces as training data.

12 Claims, 11 Drawing Sheets

(52) U.S. Cl.
CPC ............... *G06T 2207/10056* (2013.01); *G06T 2207/20081* (2013.01); *G06T 2207/30136* (2013.01)

(58) Field of Classification Search
CPC . G06T 2207/10056; G06T 2207/20081; G06T 2207/30136
See application file for complete search history.

(56) References Cited

U.S. PATENT DOCUMENTS

| | | | |
|---|---|---|---|
| 2019/0112694 A1 | 4/2019 | Takagi et al. | |
| 2019/0295015 A1* | 9/2019 | Kosaka | G06Q 10/1097 |
| 2020/0110025 A1 | 4/2020 | Yacoubian | |
| 2020/0193337 A1 | 6/2020 | Teranishi | |

FOREIGN PATENT DOCUMENTS

| | | | | |
|---|---|---|---|---|
| JP | 2005-315703 A | | 11/2005 | |
| JP | 2008-7809 A | | 1/2008 | |
| JP | 2018072214 A | * | 5/2018 | |
| JP | 2019-12037 A | | 1/2019 | |
| JP | 2019-168844 A | | 10/2019 | |
| JP | 2020-98435 A | | 6/2020 | |
| JP | 2020-139915 A | | 9/2020 | |
| RU | 2317540 C2 | * | 2/2008 | |
| WO | WO-2007116599 A1 | * | 10/2007 | ............. C22C 38/02 |
| WO | WO 2014/033928 A1 | | 3/2014 | |
| WO | 2017175739 A1 | | 10/2017 | |

OTHER PUBLICATIONS

Gajalakshmi et al., "Grain size measurement in optical microstructure using support vector regression" (Year: 2017).*

"Grain Size Analysis of Metal Texture", Sokushiri [Online], Aug. 4, 2020 (Date of Archive by InternetArchive WayBackMachine), Keyence Corporation, [Dec. 15, 2022 search], The Internet<URL:https://web.archive.org/web/20200804085346/https://www.keyence.co.jp/ss/imagemeasure/sokushiri/news/012/>, 5 pages.

International Search Report (with English translation of Categories of Cited Documents) issued on Nov. 24, 2020 in PCT/JP2020/035524 filed on Sep. 18, 2020, 5 pages.

Gajalakshmi, K. et al., "Grain size measurement in optical microstructure using support vector regression," Optik, vol. 138, 2017, pp. 320-327.

* cited by examiner

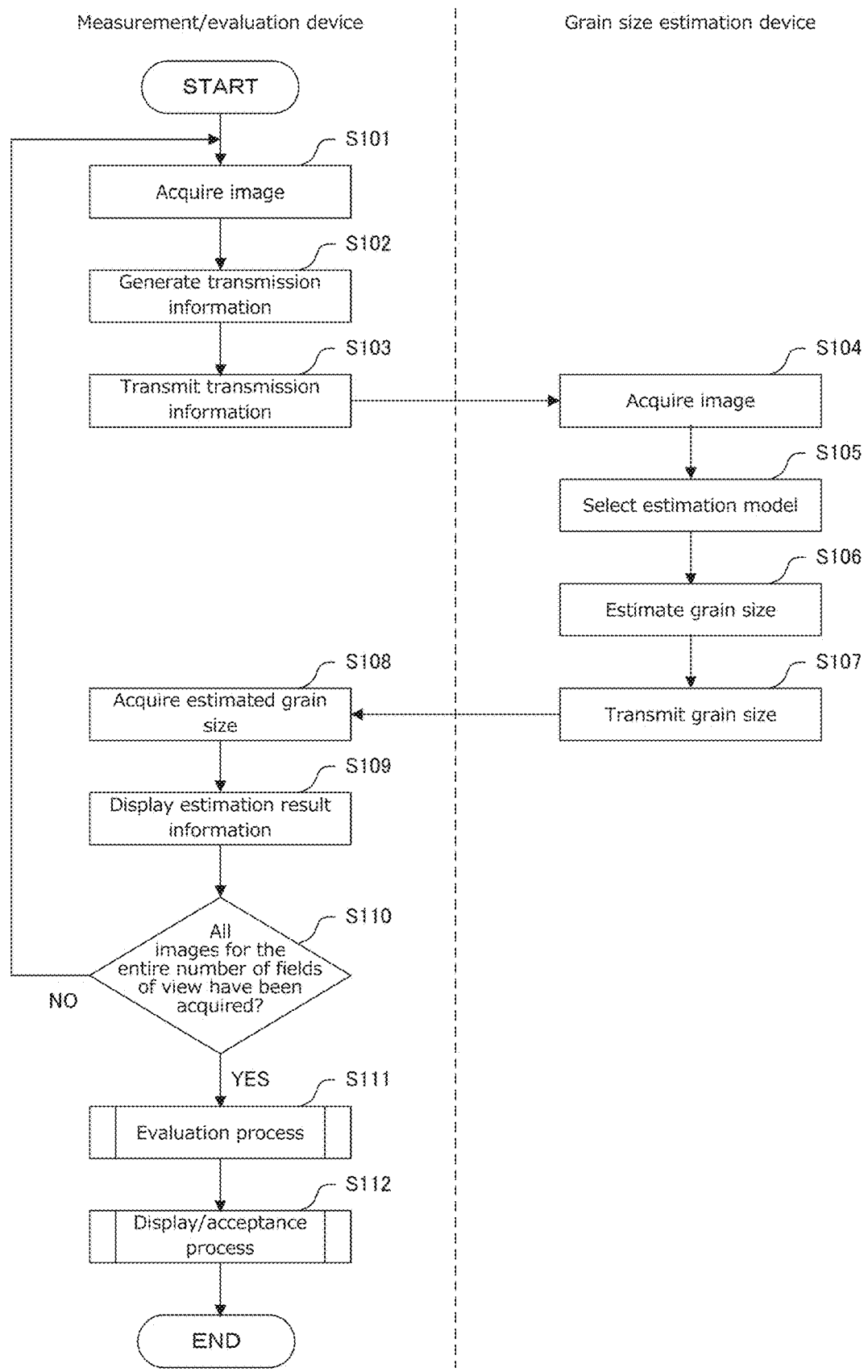

FIG.8

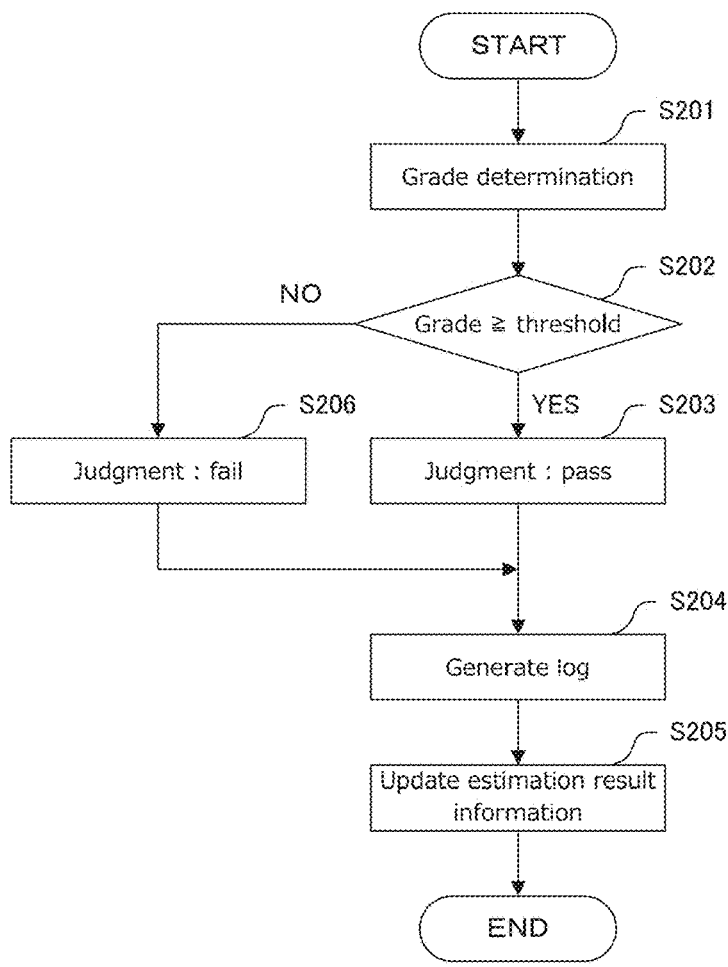

FIG.9

Evaluation result          Operator's name : www

| No. | Lot number | Version | Number of fields of view | Grade | Standard deviation σ | Pass/ fail result |
|---|---|---|---|---|---|---|
| 1 | AAAAAAAA | 0 | 20 | 8.5 | 0.2 | Pass |
| | Rev 0: automatic inspection | | | | | |
| 2 | AAAAAAAA | 0 | 20 | 8.0 | 1.3 | Pass |
| | Rev 1: operator changed grain size from yyy to zzz for field of view number xxx and re-evaluated | | | | | |
| 3 | BBBBBBBB | 0 | 20 | 7.5 | 2.4 | Fail |
| | Rev 0: automatic inspection | | | | | |
| 4 | CCCCCCCC | 0 | 20 | 8.0 | 1.0 | Pass |
| | Rev 0: automatic inspection | | | | | |
| | | | Average | 8.0 | | |

GRAIN SIZE ESTIMATION DEVICE, GRAIN SIZE ESTIMATION METHOD, GRAIN SIZE ESTIMATION PROGRAM, AND GRAIN SIZE ESTIMATION SYSTEM

FIELD

Embodiment described herein relate generally to a technique for estimating the grain size of metals such as steel.

BACKGROUND

In steel manufacturers, metallographic inspection is performed to assure the quality of shipped steel products. In metallographic inspection, the inspector uses a microscope to visually inspect a specimen cut out from a steel product to check the type and amount of non-metallic inclusion and grain sizes of the steel. When determining the grain size (grade determination), it is common to compare the specimen with the standard diagram specified by JIS (Japanese Industrial Standards) to determine the grain size number.

BRIEF DESCRIPTION OF THE DRAWINGS

FIG. 7 is a flowchart showing the metallographic evaluation method according to an embodiment.

FIG. 8 is a flowchart showing the evaluation process.

FIG. 9 shows a log.

DETAILED DESCRIPTION

In metallographic inspection, grain size of a metallographic structure in an extremely microscopic field of view is visually observed and determined, so the determination is highly dependent on the knowledge and experience of the inspector. When an inspector with such knowledge and experience retires, it is difficult to pass on his/her skills. Therefore, standardization of the inspection process has been desired which do not depend on the skills of individual inspectors. According to one embodiment, a grain size estimation device includes an acquisition unit that acquires a captured image of a surface segment of an object including metal; and an estimation unit that estimates a grain size of the surface segment of the object indicated in the acquired image, based on a predictive model generated by machine learning using images of metal surfaces and grain sizes in the metal surfaces as training data. Some embodiments of the present invention will now be described with reference to the drawings.

(Overall Configuration)

Figure 1:
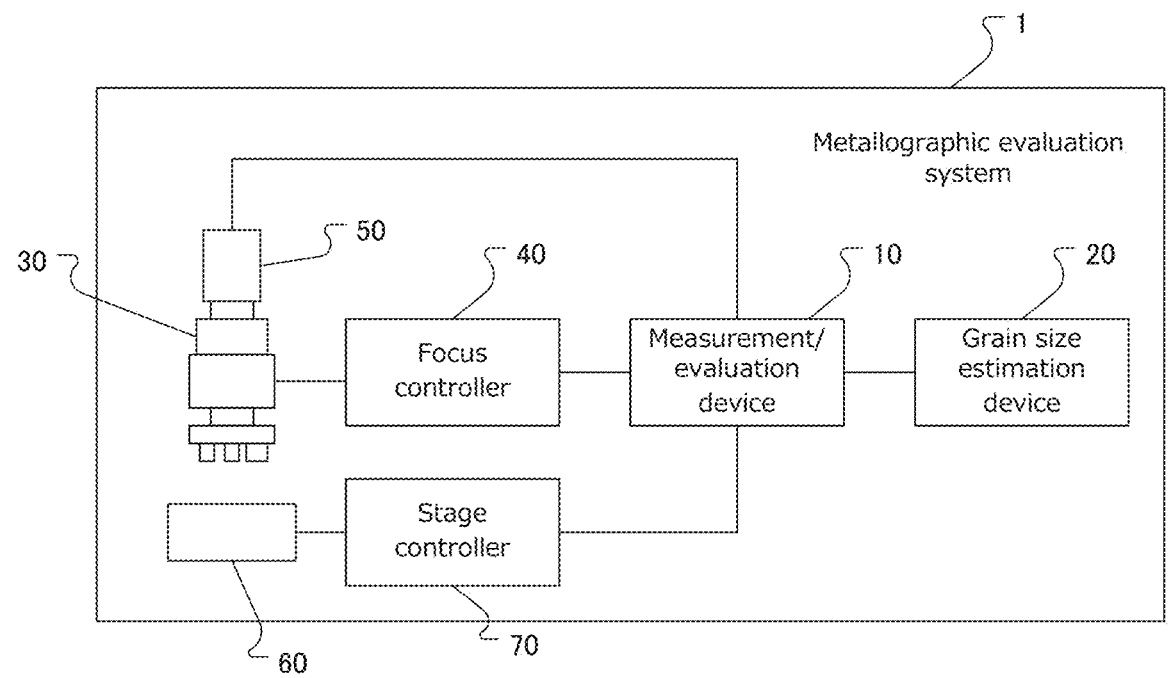
FIG. 1 shows a schematic diagram of the hardware configuration of the metallographic evaluation system according to an embodiment.

The overall configuration of the metallographic evaluation system according to the present embodiment will be described. FIG. 1 is a schematic diagram of the overall configuration of the metallographic evaluation system according to the present embodiment.

The metallographic evaluation system 1 evaluates a specimen of a predetermined shape cut out from steel, the target of the evaluation, based on the shape (condition) of the metallographic structure on its surface, and the obtained evaluation is the evaluation of the target. Specifically, the metallographic evaluation system 1 captures images of the metallographic structure at multiple segments on the surface of the specimen, estimates the grain sizes of the metallographic structure shown in the plurality of captured images, and evaluates the specimen.

As shown in FIG. 1, the metallographic evaluation system 1 includes a measurement/evaluation device 10, a grain size estimation device 20, a microscope 30, a focus controller 40, a camera 50, an X-Y stage 60, and a stage controller 70.

The measurement/evaluation device 10 is connected to the microscope 30, focus controller 40, and camera 50 in a communicable manner, and is an information processing device such as a PC (personal computer) that accepts the operator's operation and controls them. The measurement/evaluation device 10 is also communicably wire-connected to the grain size estimation device 20, and performs acquisition and image processing of the captured images of the specimen, transmission of the captured images to the grain size estimation device 20, acquisition of the estimated grain sizes that indicate the result of grain size estimation from the grain size estimation device 20, and evaluation of the specimen based on the estimated grain sizes.

The grain size estimation device 20 estimates the grain sizes of the metallographic structure shown in the captured images acquired from the measurement/evaluation device 10 based on the predictive model it possesses, and transmits the estimated grain sizes to the measurement/evaluation device 10. The predictive models are generated by machine learning based on training data, which will be described later. The machine learning in this embodiment is a supervised machine learning in which, for example, a data set including images of the metallographic structure on a surface of a metal, preferably a steel of the same type (same composition) as the steel to be evaluated, and the grain sizes of the metallographic structure indicated in the images are given as the training data.

The microscope 30 is preferably a light microscope with an auto-focus function, and is used to magnify the image of a specimen placed on the X-Y stage 60 at a predetermined magnification for the camera 50 to capture. The microscope 30 has, for example, a motorized revolving nosepiece with a plurality of objective lenses of 5×, 10×, 20×, 40× magnifications, etc., that can be attached, detached, and interchanged as needed, and an in-line illuminator that illuminates the specimen through the objective lens. The motorized revolving nosepiece and illuminator can be controlled by the measurement/evaluation device 10.

The focus controller 40 chives the motorized revolving nosepiece of the microscope 30 to select an objective lens, or moves the objective lens up and down to adjust the focus, according to the control signals received from the measurement/evaluation device 10.

The camera 50 is a camera with a color area sensor, which is connected to the microscope 30 via an adapter with a built-in relay lens and is also connected to the measurement/evaluation device 10 for image transmission. The measurement/evaluation device 10 makes the camera 50 capture the images of the specimen placed on the X-Y stage 60 and receives the captured images.

The X-Y stage 60 includes a sample holder that can hold a specimen on its top surface. The X-Y stage 60 can horizontally translate the specimen together with the holder in the X and Y directions to sequentially bring each of the plurality of measurement segments of the specimen under the objective lens's field of view for imaging by the camera 50. The horizontal translation of the holder by the X-Y stage 60 can be controlled by the measurement/evaluation device 10. An alternative configuration may be employed where the horizontal translations of the holder are manually controlled with an analog joystick. The X-Y stage 60 and the microscope 30 may preferably be placed together in a clean bench whose inside is maintained clean in order to prevent dust or other stuff from contaminating the specimens.

The stage controller 70 controls the horizontal translations of the sample holder on the X-Y stage 60 according to the control signals received from the measurement/evaluation device 10.

(Hardware Configuration)

Figure 2:
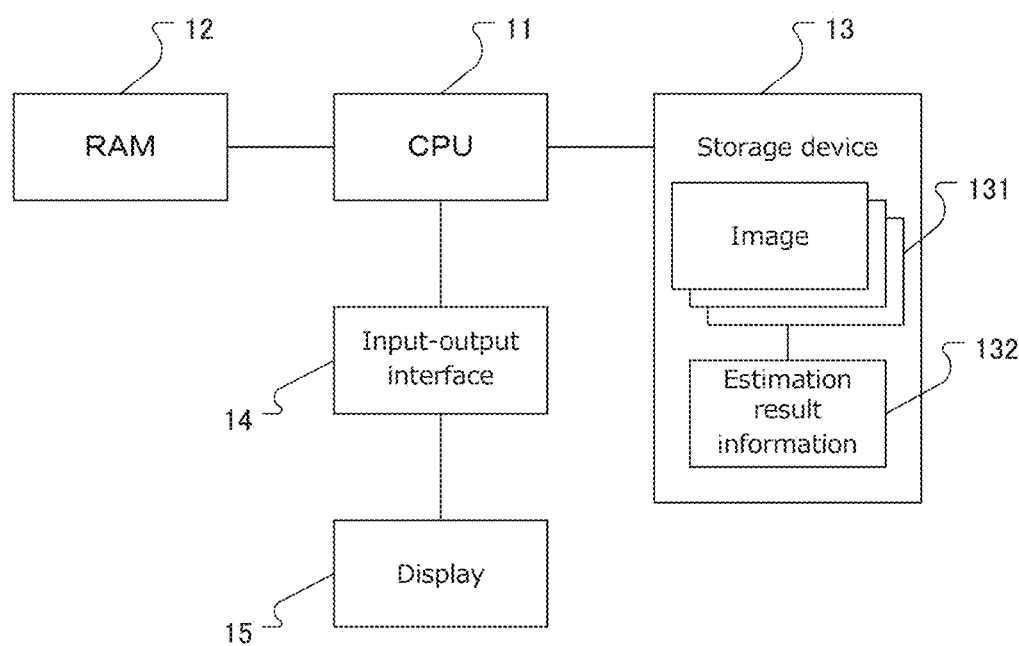
FIG. 2 is a block diagram showing the hardware configuration of the measurement/evaluation device.
Figure 3:
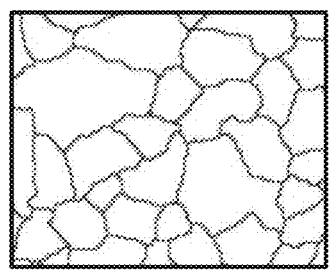
FIG. 3 shows a captured image.

The hardware configuration of the measurement/evaluation device 10 is described. FIG. 2 is a block diagram of the hardware configuration of the measurement/evaluation device. FIG. 3 shows a captured image. As shown in FIG. 2, the hardware of the measurement/evaluation device 10 includes a CPU (Central Processing Unit) 11, RAM (Random Access Memory) 12, storage device 13, Input-output I/F (Interface) 14, and display 15.

The CPU 11 and RAM 12 work together to execute various functions described below, and the storage device 13 stores various data used in the processes executed in various functions. Input-output I/F 14 inputs and outputs data and control signals to and from the above-mentioned microscope 30, focus controller 40, camera 50, and stage controller 70. Input-output I/F 14 also inputs and outputs data to and from external devices connected to the measurement/evaluation device 10 such as the display 15 that displays estimation result windows and the likes to be described later, input devices such as a mouse and keyboard (not shown in the drawings), external storage devices, and output devices such as a video hard copy and a printer, as well as the grain size estimation device 20.

In this embodiment, the storage device 13 stores a plurality of captured images 131 acquired in the metallographic evaluation method described below, and estimation result information 132 corresponding to the plurality of captured images 131.

As shown in FIG. 3, the captured images 131 capture predetermined measurement segments on a surface of a specimen, which in this embodiment is images of the metal's microstructure. Grain size numbers are estimated from the fineness of the metallographic structure shown in the captured images 131.

The estimation result information 132 is a set of data generated by the metallographic evaluation method and includes information on the predictive model used, an estimated grain size corresponding to one captured image 131, a result of the pass/fail determination of a specimen based on the estimated grain size, a grain number distribution and confidence distribution based on the estimated grain size, and so on. The estimation result information 132 includes a log that includes the history of changes made to the estimation result information 132.

Figure 4:
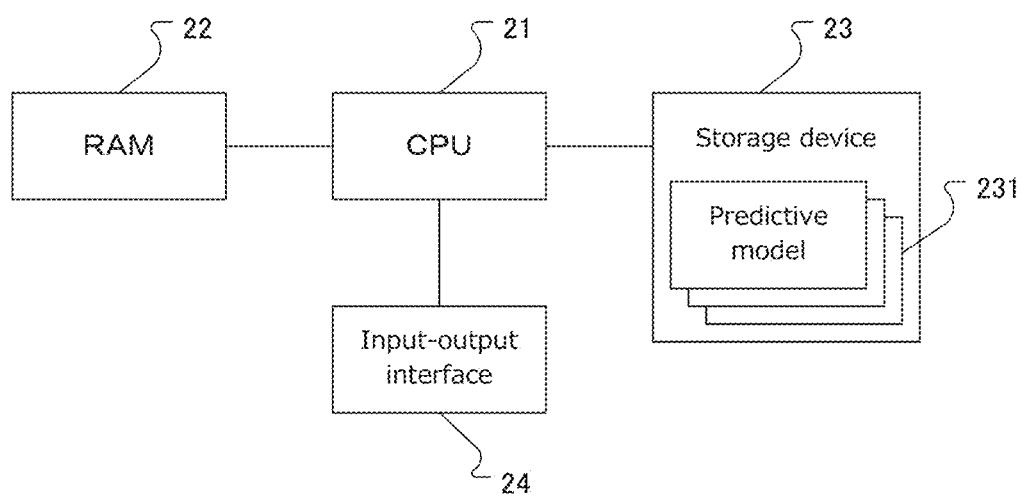
FIG. 4 shows a block diagram of the hardware configuration of the grain size estimation device.

The hardware configuration of the grain size estimation device 20 is described. FIG. 4 shows a block diagram of the hardware configuration of the grain size estimation device 20.

As shown in FIG. 4, the hardware of the grain size estimation device 20 includes a CPU (Central Processing Unit) 21, RAM (Random Access Memory) 22, a storage device 23, and an input-output I/F (interface) 24. The CPU 21 and RAM 22 work together to execute various functions described below, and the storage device 23 stores various data used in the metallographic evaluation method executed in the various functions. The input-output I/F 24 performs input and output of data to and from the measurement/evaluation device 10. The input-output I/F 24 may also perform input and output of data to and from external devices such as input devices such as a mouse and keyboard, a display, external storage devices, and output devices such as a printer.

In this embodiment, a plurality of predictive models 231 described above is stored in the storage device 23. The plurality of prepared predictive models 231 may be those, for example, built for each type of metal material (type of steel) or those built using training data that are all or partially different from each other. The multiple predictive models 231 are managed with AI model IDs that uniquely identify each of them.

(Functional Configuration)

Figure 5:
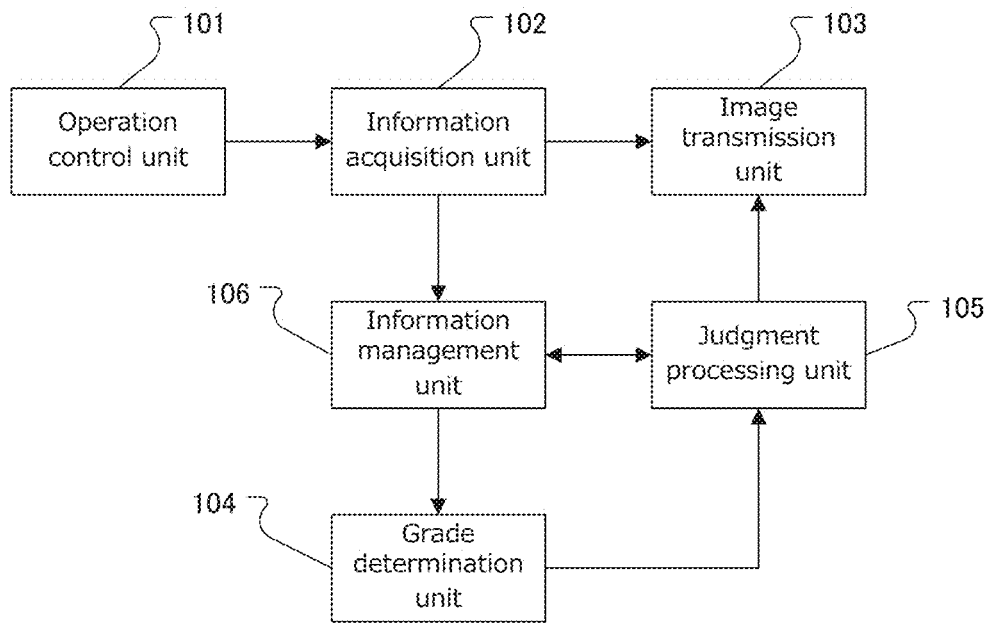
FIG. 5 is a block diagram of the functional configuration of the measurement/evaluation device.

The functional configuration of the measurement/evaluation device 10 is described. FIG. 5 is a block diagram of the functional configuration of the measurement/evaluation device. As shown in FIG. 5, the functional units of the measurement/evaluation device 10 includes an operation control unit 101, an information acquisition unit 102, an image transmission unit 103, a grade determination unit 104, a determination processing unit 105, and an information management unit 106.

The operation control unit 101 controls the operations of the illuminator, the camera 50, the motorized revolver via the focus controller 40, and the X-Y stage 60 via the stage controller 70. The information acquisition unit 102 acquires captured images 131 from the camera 50 and estimated grain sizes from the grain size estimation device 20. The image transmission unit 103 transmits transmission information including the captured image 131 and AI model ID to the grain size estimation device 20, wherein a unique field of view number is attached to each captured image 131. The field of view number will be described later.

The grade determination unit 104 determines a grade for a specimen based on the acquired estimated grain sizes. The determination processing unit 105 performs various determinations in the metallographic evaluation method described below. The information management unit 106 manages the estimation result information 132 and logs generated by the metallographic evaluation method. For example, the information management unit 106 displays an estimation result window showing the estimation result information 132 on the display 15, accepts operations from operators, and generates or updates a log thereof and updates the estimation result information 132 when an editing is done by the operator.

Figure 6:
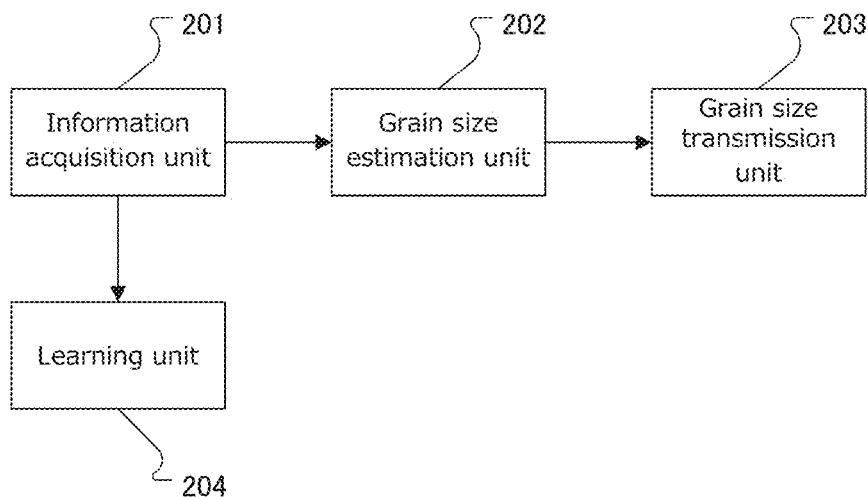
FIG. 6 is a block diagram showing the functional configuration of the grain size estimation device.

Next, the functional configuration of the grain size estimation device 20 will be explained. FIG. 6 is a block diagram of the functional configuration of the grain size estimation device. As shown in FIG. 6, the functional units of the grain size estimation device 20 includes an information acquisition unit 201, a grain size estimation unit 202, a grain size transmission unit 203, and a learning unit 204.

The information acquisition unit 201 acquires transmitted information and training data for performing machine learning from the measurement/evaluation device 10. The grain size estimation unit 202 estimates the grain size of the metallographic structure shown in the captured image 131 included in the acquired transmitted information by the predictive model 231 identified by the AI model ID.

The grain size transmission unit 203 transmits the grain size (estimated grain size) estimated by the grain size estimation unit 202 to the measurement/evaluation device 10 in combination with the field of view number assigned to the captured image 131 for which the grain size estimation was made. When the information acquisition unit 201 acquires a training data, the learning unit 204 performs a training using the training data to update the predictive model 231 associated with the training data. When an instruction to generate a new predictive model is included in the training data, a new predictive model is generated using the training data.

(Metallographic Evaluation Method)

The metallographic evaluation method performed by the metallographic evaluation system 1 is described. FIG. 7 is a flowchart showing the metallographic evaluation method of this embodiment. It is assumed that, by the time a metallographic evaluation is started, a specimen has been placed on the sample holder on the X-Y stage 60, the sample holder has been returned to the home position, and the lot number (number of samples) of the specimen, version, AI model ID, and operator's name have been input to the measurement/evaluation device 10. These inputs are referred to as input information in this description.

Selecting and clicking the Home button on the display 15 of the measurement/evaluation device 10 with a pointing device such as a mouse will drive and control the X-Y stage 60 via the stage controller 70 and return the sample holder to the home position. The process flow starts when the start button in the metallographic evaluation method displayed on the display 15 is clicked.

When the start button is clicked, the operation control unit 101 of the measurement/evaluation device 10 drives and controls the X-Y stage 60, and the information acquisition unit 102 acquires a captured image 131 of the surface of the specimen taken by the camera 50 (S101). In the metallographic evaluation method of this embodiment, the captured images 131 for the preset number of fields of view are acquired until the YES determination is made in the determination processing of step S110 described below. But, at first, the image of one field of view is captured. The number of fields of view means the number of surface segments to be imaged for one specimen. For example, when the number of fields of view is 20, two rows by ten columns of surface segments with different positions on the specimen are captured and that makes a total of twenty captured images 131. The number of fields of view may be changed as needed, but it is preferable to select the number in accordance with the JIS standards.

As the image is captured with translating the X-Y stage 60 horizontally on which the sample holder is placed, the captured images are stored in the storage device 13 together with the respective positions of the surface segments on the specimen. The positions of the surface segments, or fields of view, are different from each other and are identified with the field of view numbers. In other words, the field of view numbers are the information that uniquely identify the captured images 131.

After acquiring an captured image of one field of view, the image transmission unit 103 combines the captured image 131, the field of view number and an AI model ID (S102) to generate a transmission information. After generating the information, the image transmission unit 103 transmits the transmission information to the grain size estimation device 20 (S103). After the transmission, the measurement/evaluation device 10 waits for the result response of the estimated grain size from the grain size estimation device 20.

The information acquisition unit 201 of the grain size estimation device 20 acquires the transmission information (S104). After the acquisition, the grain size estimation unit 202 selects the predictive model 231 identified by the AI model ID included in the transmission information (S105), and, using the selected predictive model, estimates the grain size of the metallographic structure from the captured image 131 of one field of view included in the transmission information (S106). If no predictive model corresponding to the acquired AI model ID exist, an error is sent to the measurement/evaluation device 10 from the grain size transmission unit 203. If the captured image 131 is unclear or otherwise not fit for estimating the grain size, the estimated grain size is treated as unknown.

After the estimation, the grain size transmission unit 203 transmits the estimated grain size to the measurement/evaluation device 10 (S107). After the transmission, the information acquisition unit 102 of the measurement/evaluation device 10 acquires the estimated grain size (S108), and the information management unit 106 generates an estimation result information 132, which will be described in detail later, based on the acquired estimated grain size, the captured image of one field of view corresponding to the estimated grain size, the field of view number corresponding to the captured image, etc., and displays the estimation result information 132 on the display 15 (S109) and manages it. If the estimation result information 132 for the current specimen has been generated in advance, the information is updated.

After displaying the information, the determination processing unit 105 determines whether or not all the captured images for the total number of fields of view have been acquired. The determination may be made based on whether the field of view number of an acquired image has reached a predetermined count of fields of view, although the determination may be made based on different criteria. When it is determined that the images for the entire number of fields of view have been acquired (S110, YES), the evaluation process is executed (S111), which will be described in detail later. After the evaluation process, the information management unit 106 displays an estimation result window showing the estimation result information 132 on the display 15, and a display/acceptance process is executed to accept input from the operator (S112). Details of the display/acceptance process and the estimation result window displayed on the display 15 will be described later.

On the other hand, if it is determined that the images for the total number of fields of view have not been acquired (S110, NO), the process goes to the step of acquiring captured images at step S101. In this step, the X-Y stage 60 is moved to another surface segment where no image has been captured yet and an captured image is captured there.
(Evaluation Process)

Next, the evaluation process is described. FIG. 8 is a flowchart showing the evaluation process. As shown in FIG. 8, the grade determination unit 104 determines the grade of the specimen based on the plurality of acquired estimated grain sizes (S201). The grade may be either the average of the plurality of estimated grain sizes or the lowest size among the plurality of estimated grain sizes. In this embodiment, the grade is the average of the estimated grain sizes. After determining the grade, the determination processing unit 105 determines whether the determined grade is above a predetermined threshold (S202) or not. The threshold may be suitably chosen according to the type of the steel or the purpose the steel is used for.

If the grade is determined to be above a predetermined threshold (S202, YES), the determination processing unit 105 assigns a pass to the pass/fail result for the current Rev (S203). Rev (Revision) is a number generated in such a way that the initial number starts from Rev 0, and the number is incremented every time some estimated grain sizes are removed or changed in the display/acceptance process, which will be described later, and the evaluation process is executed again. In other words, Rev is the identification number of the estimation result information 132. The Rev number is incremented every time the evaluation process is performed on a same specimen, but when a first evaluation process is performed for a different specimen, that is, when the metallographic evaluation is performed for a second time, the Rev number is set to zero.

After a pass is assigned, the information management unit 106 generates a log for the current Rev based on the pass/fail result, input information, and a plurality of estimated grain sizes (S204), and stores it in the storage device 13.

As shown in FIG. 9, the log includes the operator's name, lot number, version, number of fields of view, grade, standard deviation σ for each estimated grain size, pass/fail determination result, and average of the grades, and is updated every time the evaluation process is executed. Every change is listed in the log with respective Rev numbers. As shown in the row of Rev 0, various information cannot be edited as Rev 0. For example, every time the estimation result information 132 of Rev 0 is modified and the evaluation process is executed, a new estimation result information 132 is generated and the Rev number is incremented to Rev 1 and then to Rev 2, etc. In FIG. 9, the row No. 2 with Rev 1 shows that the operator changed the grain size from yyy to zzz for the field of view number xxx, and the evaluation process was executed again, and although the grade decreased by 0.5, it was determined as pass in the pass/fail determination.

The log containing such pass/fail determinations can be printed with a printer and used as a report. However, it may be preferable that the rows in the log including changes with incremented Rev numbers are encrypted and hidden so that only the system administrators are given the privileges to access them. As the log is updated and managed in this way every time the evaluation process is executed, data tampering or other foul conducts can be prevented.

The Rev numbers can be in either the confirmed state or the unconfirmed state depending on the operation of the Confirm Rev button (see FIG. 13), which will be described later. When an estimation result information 132 with an unconfirmed Rev number is modified, the Rev number is not incremented.

After generating the log, the information management unit 106 updates the estimation result information 132 based on the input information, transmission information, estimated grain size, and log (S205), and the process ends.

On the other hand, if the grade is determined to be less than the predetermined threshold (S202, NO), the determination processing unit 105 assigns a fail as the pass/fail determination result to the current Rev (S206) and goes to the generation of the log at step S204.
(Display/Acceptance Process)

Figure 10:
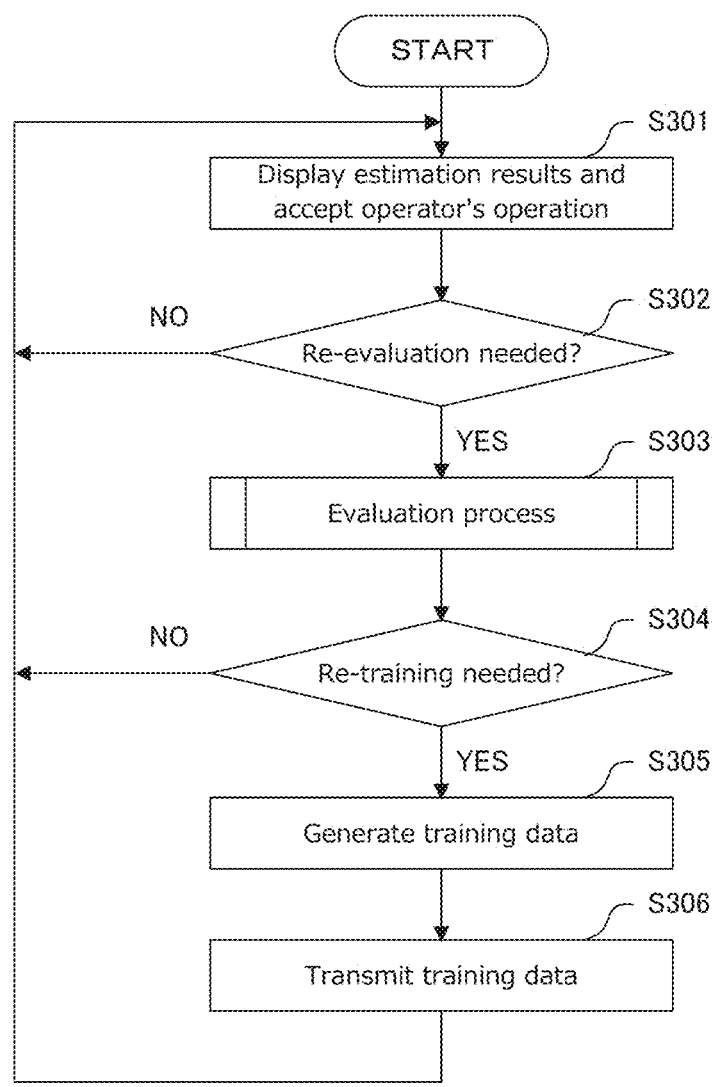
FIG. 10 is a flowchart showing the display/acceptance process.

The display/acceptance process is described. FIG. 10 is a flowchart showing the display/acceptance process. As shown in FIG. 10, the information management unit 106 displays the estimation result window (see FIG. 12) on the display 15 and accepts the operator's operation (S301). The estimation result window will be described later. The accepted operator's operations are operations for the estimation result window including displaying of a report (log) that includes the distribution of the grain size numbers, confidence distribution, and pass/fail determination results, and removing or changing of the estimated grain size associated with an arbitrary field of view number, etc.

Next, the determination processing unit 105 determines whether or not a re-evaluation is needed (S302). The determination determines that a re-evaluation is needed when the estimated grain size number (a value for the grain size) associated with a given field of view number is removed or changed. The estimation result window works in such a way that each captured image 131 can be viewed and each estimated grain size can be removed or modified. If the operator checks a captured image 131 and finds that the estimated grain size associated with the field of view number for a captured image 131 is wrong, he/she can remove or change the estimated grain size.

If a determination is made that re-evaluation is not needed (S302, NO), the process goes to step S301 and the display of the current estimation result window is maintained. On the other hand, if a determination is made that re-evaluation is needed (S302, YES), the evaluation process is executed again (S303). When the evaluation is executed again, if the estimated grain size was removed, the evaluation is executed without the removed estimated grain size, and if the estimated grain size was changed, the evaluation is executed including the changed estimated grain size.

After the evaluation process is executed, the determination processing unit 105 determines whether or not to make the grain size estimation device 20 perform a retraining, that is, updating of the predictive model (S304). In this determination, the determination to execute a retraining is made when an estimated grain size is changed, for example. The estimated grain size is changed when the operator finds that estimated results given by a selected predictive model 231 are not correct. Therefore, the accuracy of the predictive model 231 can be improved by executing the retraining in such cases. Alternatively, instead of such an automatic determination, the operator may manually instruct whether or not to execute a retraining.

If it is determined that a retraining is to be performed (S304, YES), the image transmission unit 103 generates a training data by associating the changed estimated grain size, the captured image 131 associated with the estimated grain size, and the selected AI model ID (S305) and transmits the training data to the grain size estimation device 20 (S306). After the transmission, the system goes to step S30 1and maintains the display of the current estimation result window. On acquiring the training data, the grain size estimation device 20 executes the retraining process described below.

Alternatively, the display/acceptance process described above may also be performed during the process of displaying the estimation result information in step S109 of the flowchart in FIG. 7.

(Retraining Process)

Figure 11:
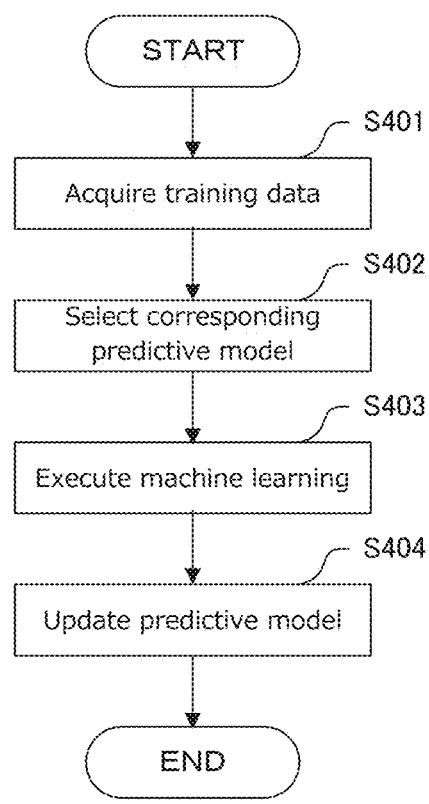
FIG. 11 is a flowchart showing the retraining process.

The retraining process is described. FIG. 11 shows a flowchart of the retraining process. As shown in FIG. 11, when the information acquisition unit 201 acquires a training data (S401), the learning unit 204 takes the AI model ID included in the training data and selects the predictive model 231 (S402) identified with the ID. Then, the selected predictive model 231 is loaded and a training is executed using the acquired training data (S403), and when the predictive model 231 is updated by machine learning (S404), the process ends.

(Various Windows)

Various windows displayed on the display 15 as the estimation result information 132 after the evaluation process are described. FIGS. 12 to 15 show the estimation result window, Rev Edit window, grain size number distribution window, and confidence distribution window displayed on the display, respectively.

Figure 12:
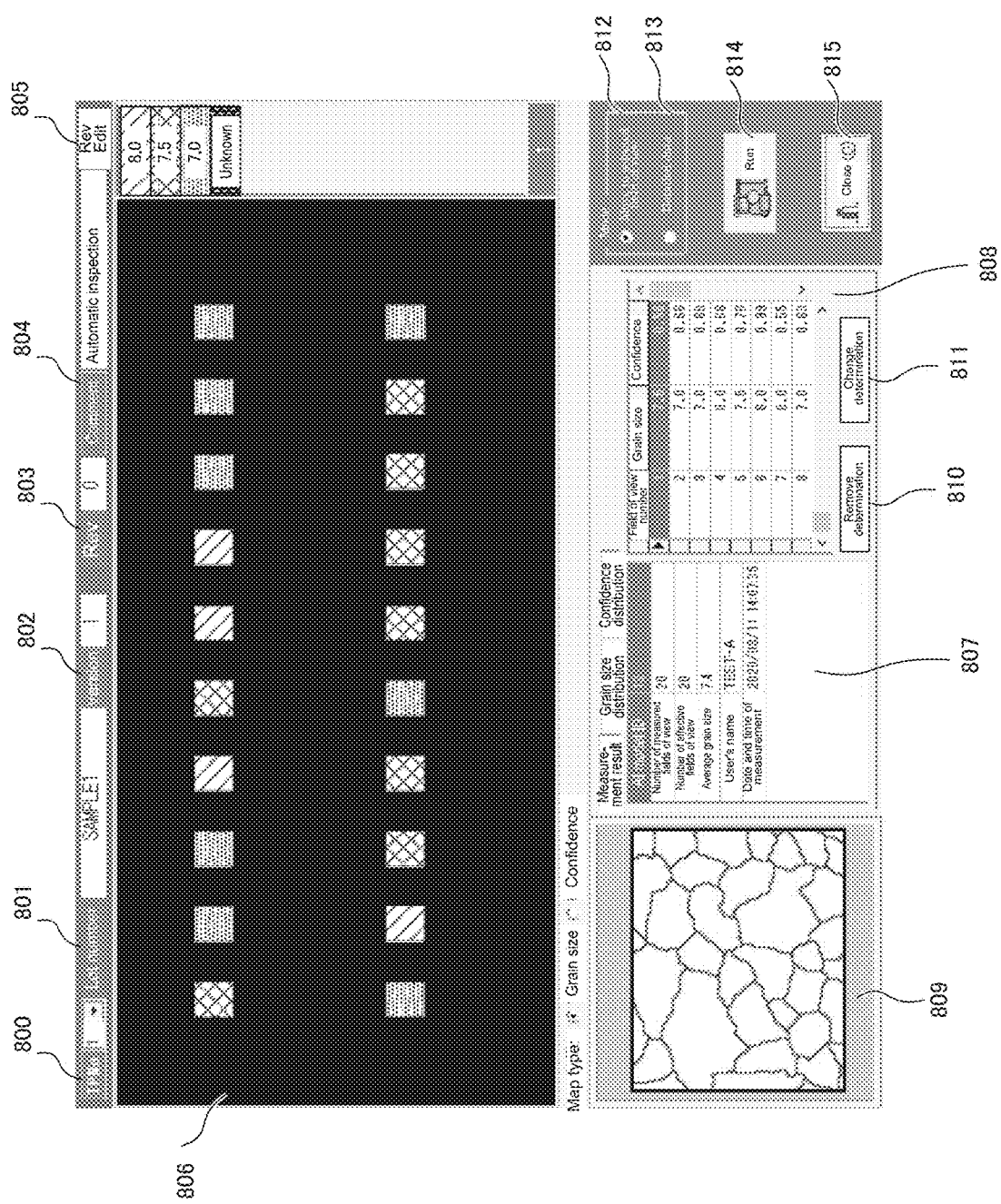
FIG. 12 shows the estimation result window shown on the display.

As shown in FIG. 12, the estimation result window includes a TP No. box 800, a Lot number box 801, a Version box 802, a Rev box 803, a Comment box 804, and a Rev Edit button 805 in the upper part, and a Map type 806 in the lower part. The TP No. box 800 is used to select a sample number for checking the estimation result information 132, and all of the sample numbers can be selected for which the evaluation process has been completed, including the specimen currently set in the sample holder. The Lot number box 801 and the Version box 802 show the numbers corresponding to the TP No. indicated in the TP No. box 800. The Rev box 803 shows the current Rev number of the selected specimen, and the Comment box 804 shows the comment associated with the Rev number.

Figure 13:
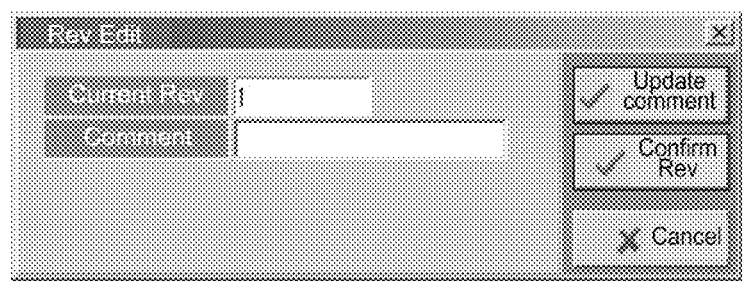
FIG. 13 shows the rev edit window shown on the display.

As shown in FIG. 13, a click on the Rev Edit button 805 displays a window that includes the currently displayed Rev number and a Comment box showing the comment associated with the current Rev number. The Comment box can be edited and updated by the operator manually entering a comment for the current Rev number and clicking the Update Comment button. The updated comment is displayed in the Comment box 804 shown in FIG. 12. The Cancel button is used to discard the currently edited contents and close the window.

Clicking the Confirm Rev button confirms the unconfirmed Rev number and closes the window wherein the current content in the Comment box is also updated at the same time. In the present embodiment, the estimation result information 132 with Rev 1 and later is initially in the unconfirmed state, and the operator's click on the Confirm Rev button at any time confirms the estimation result information 132 (especially the estimation result, grade, and pass/fail determination result) as well as the Rev number.

In the operation described above, if any field of view data is deleted in the estimation result information 132 with Rev n (n>0) in the unconfirmed state, the evaluation process is performed again and the estimation result information 132 is updated without incrementing Rev n, and the estimation result information 132 before the deletion is deleted. On the other hand, if any field of view data is deleted in the estimation result information 132 with Rev n (n>0) in the confirmed state, the evaluation process is performed again and the estimation result information 132 is updated with incrementing the Rev to n+1 with the unconfirmed state. This is also the case when the estimated grain size is changed. If the evaluation process is executed in the main window, not shown in the figures, the system may hold the new estimation result information 132 with Rev 0 after discarding all of the estimation result information 132 with any Rev numbers.

As shown in FIG. 12, Map type 806 can be either the grain size number map or the confidence map. The grain size number map is displayed in FIG. 12. In the grain size number map, the estimated grain sizes (grain size numbers) are displayed in designated colors at each position of the field of view number, and on the right side of the figure, a table is shown that indicates the correspondence of colors to grain size numbers. This allows the operator to easily see at a glance the distribution of the grain size number of the current specimen. On the other hand, the confidence map shows in two colors whether the confidence value for each position of the field of view number is greater than a predetermined confidence threshold (e.g., 0.6) or not.

Figure 14:
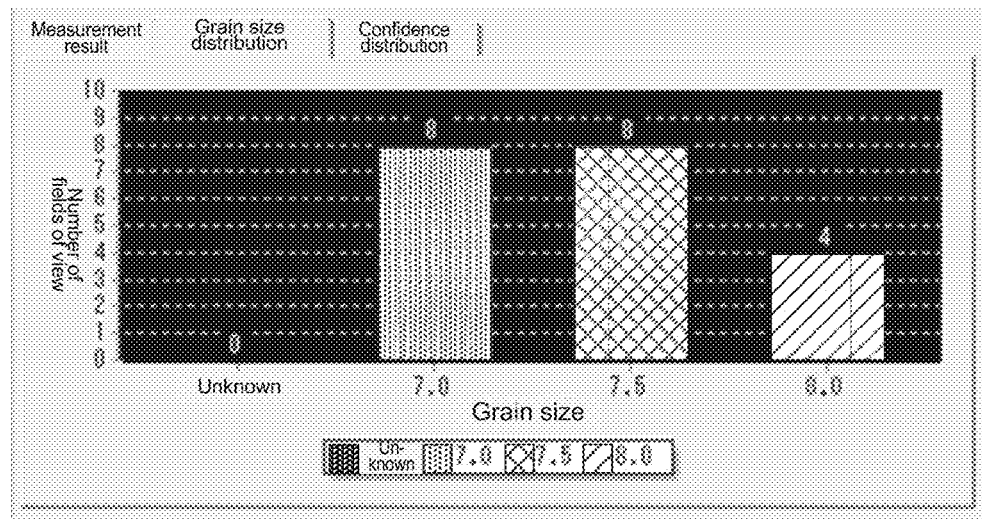
FIG. 14 shows the grain size number distribution window shown on the display.
Figure 15:
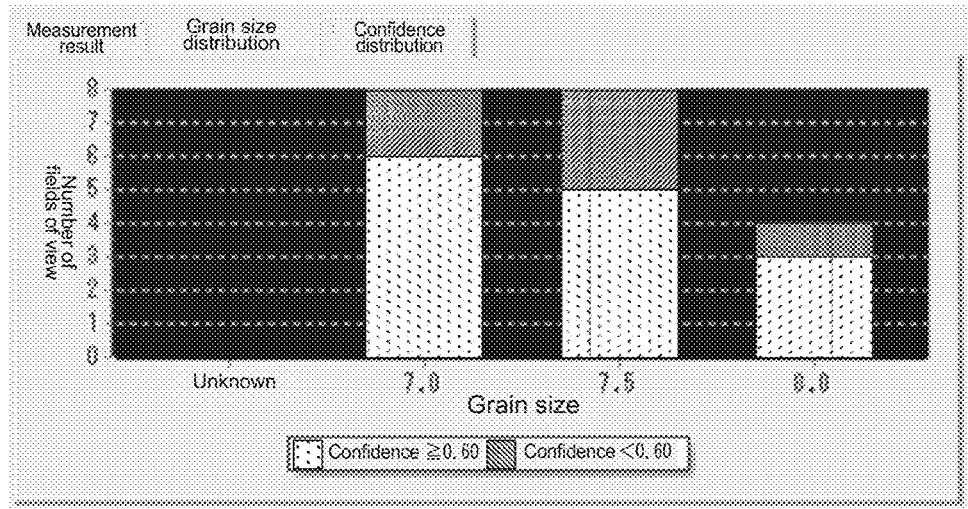
FIG. 15 shows the confidence distribution window shown on the display.

At the bottom center of the Map type 806, there is a switchable display pane 807 that includes the evaluation result tab that indicates predetermined items included in the estimation result information 132, another tab that displays the grain size number distribution, and a tab that displays the confidence distribution. The evaluation result tab has places for indicating an AI model ID, the number of measured fields of view, the number of effective fields of view, an average grain size number (grade), the user's name who did the measurement (operator's name), and the date and time the measurement was done (evaluation date and time). The grain size number distribution and the confidence distribution are displayed in a bar graph having the number of fields of view on the vertical axis and the grain size number on the horizontal axis, as shown in FIGS. 14 and 15.

On the right side of the switchable display pane 807 in FIG. 12, the field of view data selecting pane 808 is located that selectably displays the grain number and confidence value for each respective field of view number, and when the operator selects and clicks on the row of a field of view number (hereinafter referred to as the field of view data), the captured image 131 that corresponds to the selected field of view data is displayed in the image pane 809 on the left side of the figure. Below the field of view data selecting pane 808, the Remove determination button 810 and the Change determination button 811 are located.

If the operator clicks on a field of view data to select it and then the Remove determination button 810, a window appears asking the operator whether or not to perform the evaluation process again without the estimated grain size associated with the selected field of view data, and then if the operator clicks OK in the window, the determination of YES is made in the determination process described in step S302 of FIG. 10 above. Alternatively, if the operator clicks on a field of view data to select it and then the Change determination button 811, a window for inputting a new value of estimated grain size for changing appears together with another window asking the operator whether or not to execute the evaluation process again with including the changed estimated grain size and then if the operator clicks OK in the window, the determination of YES is made in the determination process described in step S302 of FIG. 10 above.

The reference number 812 in FIG. 12 is the selection button for moving the X-Y stage 60 to the field of view selected by the Map type 806 and executing the estimation determination again. The reference number 813 is the selection button for displaying the detailed data for the field of view number in the row selected in the field of view data selecting pane 808. The reference number 814 is the button to execute either one of these, and the reference number 815 is the button for closing the estimation result image for the current Rev number.

Although, the various windows have been described so far which are displayed in the display 15 for the estimation result information 132 generated after the evaluation process, it is preferable that the present functions become accessible after the measurements for all of the specimens placed on the sample holder are completed.

In the embodiment described above, the grain size of the metallographic structure in the captured image 131 can be estimated using the predictive model 231, which can estimate the grain size with high accuracy by machine learning, and thus the transfer of skills of individual inspectors are not needed, and the evaluation can be standardized. Standardizing the evaluation can eliminate differences in the determination of grain sizes between skilled and inexperienced inspectors, and thus reduces the variability of evaluation results.

Also, in this embodiment, as the log is stored and managed in the storage device 13 along with the estimation result information 132, management of inspection work records can be automated. Furthermore, in visual inspections done by human eyes, if the demand for inspection increases, the inspection will obviously take a long time, which may lead to labor problems for the inspectors. However, using the system in this embodiment, such problems may be avoided, and in the long run the costs can be lowered, too.

Figure 16:
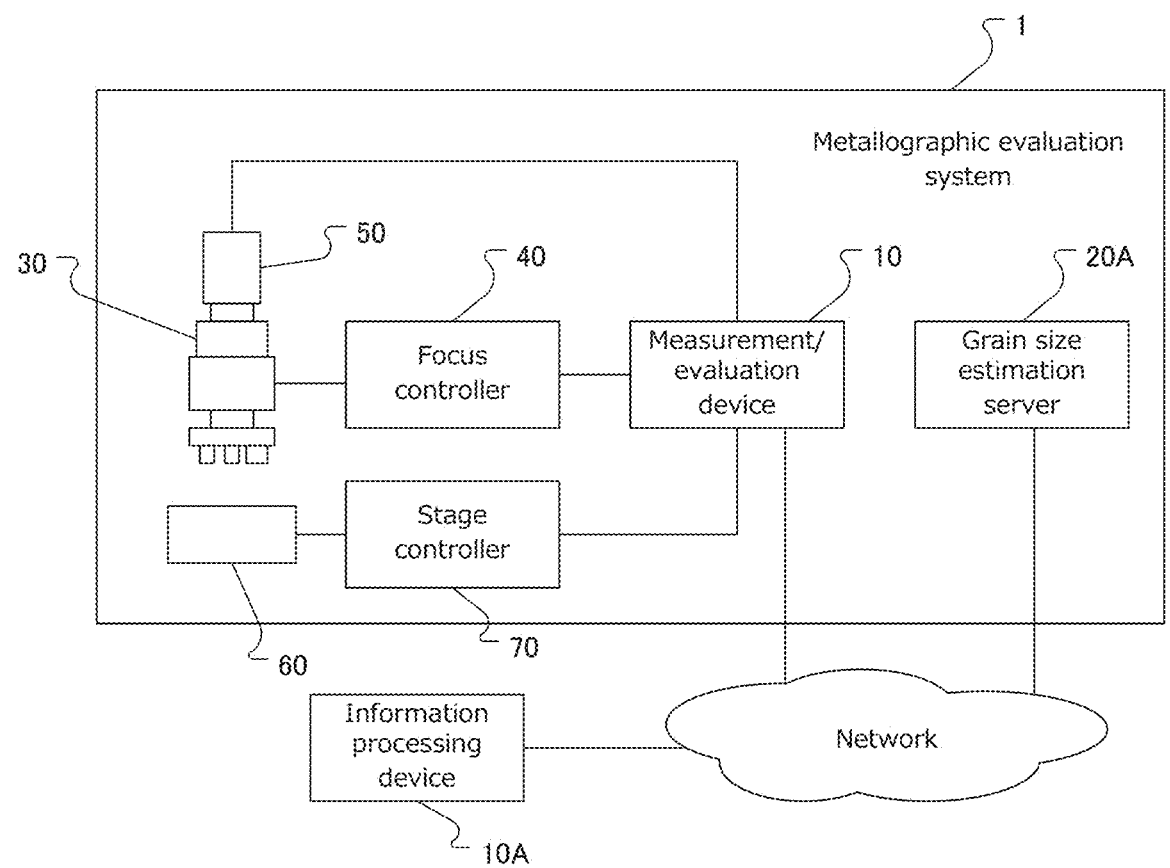
FIG. 16 shows a schematic diagram of the hardware configuration of an alternative metallographic evaluation system.

Although, the measurement/evaluation device 10 and the grain size estimation device 20 are wire-connected in the embodiment, the method of communication is not so limited. As shown in FIG. 16, the grain size estimation device 20 may be configured as a remotely located grain size estimation server 20A, and the measurement/evaluation device 10 may access the grain size estimation server 20A via a network such as the Internet or an intranet to communicate with each other. In this case, it may be preferable to allow access from multiple measurement/evaluation devices 10. For example, the grain size estimation server 20A manages user IDs and passwords, and when an operator of a measurement/evaluation device 10 enters his/her user ID and password to request an access to the grain size estimation server 20A, and after the access is approved, the transmission information is sent to the grain size estimation server 20A. With such system configurations, transmission information can be sent to the grain size estimation server 20A via a network to obtain estimated grain sizes not only from measurement/evaluation devices 10 connected to microscopes 30, etc., but also from other information processing devices 10A.

Alternatively, the metallographic evaluation system described above may be configured as a single information processing device having various functions of the measurement/evaluation device 10 and the grain size estimation device 20.

Figure 17:
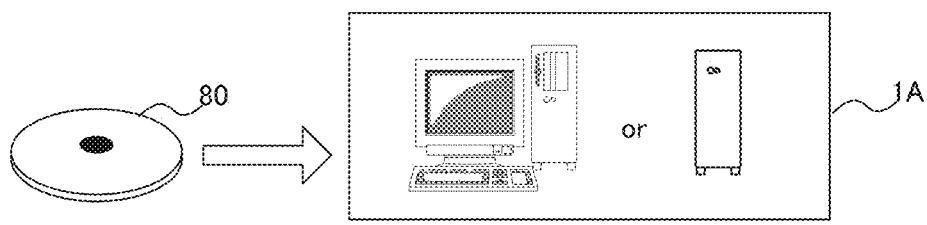
FIG. 17 shows the concept of a computer reading a storage media storing a program according to an embodiment.

In this embodiment, the measurement evaluation program that realizes various functions of the measurement/evaluation device 10 and the grain size estimation program that realizes various functions of the grain size estimation device 20 are described as the ones installed in the measurement/evaluation device 10 and the grain size estimation device 20 in advance; however, programs in the present invention also include those stored in storage media. Such storage media include the media that can be attached to and detached from devices, including magnetic tapes, magnetic disks (hard disk drives, etc.), optical disks (CD-ROMs, DVD disks, etc.), magneto-optical disks (MOs, etc.), flash memory, and other media, and the media that can be read and executed by computers that work as the measurement/evaluation device 10 or grain size estimation device 20 described above, such as media that can be accessed via a network. For example, FIG. 17 shows the concept of a computer 1A such as a PC or a server reading a measurement evaluation program and/or a grain size estimation program from an optical disk 80.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A grain size estimation device comprising:
an acquisition unit that acquires a captured image of a surface segment of an object including metal;
an estimation unit that estimates a grain size of the surface segment of the object indicated in the acquired image, based on a predictive model generated by machine learning using images of metal surfaces and grain sizes on the metal surfaces as training data; and
a determination unit that determines whether or not the object is good based on the estimation result made by the estimation unit.

2. The grain size estimation device according to claim 1 further comprising a training unit
wherein when the grain size estimated by the estimation unit is modified by a user, the training unit updates the predictive model by machine learning using the modified grain size and the captured image associated with the modified grain size as training data.

3. The grain size estimation device according to claim 1 wherein:
the acquisition unit acquires respective captured images of multiple surface segments on the object;
the estimation unit estimates respective grain size of each of the multiple surface segments on the object shown in the captured images; and
an evaluation unit determines that the object is good when an average value of the respective estimated grain sizes exceeds a predetermined threshold value.

4. The grain size estimation device according to claim 1 further comprising a presentation unit that presents a result information including an estimated grain size to a user, and
when the user changes the result information, the grain size estimation device attaches an identifying information to the changed result information that distinguishes the changed result information from the result information that is not changed.

5. The grain size estimation device according to claim 4 further comprising a memory wherein, when a user makes a change to the result information, the memory memorizes the change the user made.

6. The grain size estimation device according to claim 1 wherein:

the acquisition unit acquires respective captured images of multiple surface segments on the object;

the estimation unit estimates respective grain size of each of the multiple surface segments on the object shown in the captured images; and a result information including estimated grain sizes and a distribution of the grain sizes of each surface segment on the object is displayed on a display device.

7. A grain size estimation method
wherein a computer
acquires a captured image of a surface segment of an object including metal, and
estimates a grain size of the surface segment of the object indicated in the acquired image, based on a predictive model generated by machine learning using images of metal surfaces and grain sizes on the metal surfaces as training data, and
determines whether or not the object is good based on the estimation result made by the estimating.

8. A non-transitory computer readable medium including a grain size estimation program that makes a computer function as:
an acquisition unit that acquires a captured image of a surface segment of an object including metal,
an estimation unit that estimates a grain size of the surface segment of the object indicated in the acquired image, based on a predictive model generated by machine learning using images of metal surfaces and grain sizes on the metal surfaces as training data, and
a determination unit that determines whether or not the object is good based on the estimation result made by the estimation unit.

9. A grain size estimation system comprising:
an image capturing device that obtains a captured image by capturing an image of a surface segment of an object including metal, and
a server that is communicably connected to the image capturing device via a network, wherein the image capturing device comprises
a transmission unit that transmits the captured image to the server, and
wherein the server comprises
an acquisition unit that acquires the captured image from the image capturing device,
an estimation unit that estimates a grain size of the surface segment of the object indicated in the acquired image, based on a predictive model generated by machine learning using images of metal surfaces and grain sizes in the metal surfaces as training data, and
a determination unit that determines whether or not the object is good based on the estimation result made by the estimation unit.

10. A grain size estimation device comprising:
an acquisition unit that acquires a captured image of a surface segment of an object including metal;
an estimation unit that estimates a grain size of the surface segment of the object indicated in the acquired image, based on a predictive model generated by machine learning using images of metal surfaces and grain sizes on the metal surfaces as training data; and
a training unit,
wherein when the grain size estimated by the estimation unit is modified by a user, the training unit updates the predictive model by machine learning using the modified grain size and the captured image associated with the modified grain size as training data.

11. A grain size estimation device comprising:
an acquisition unit that acquires a captured image of a surface segment of an object including metal;
an estimation unit that estimates a grain size of the surface segment of the object indicated in the acquired image, based on a predictive model generated by machine learning using images of metal surfaces and grain sizes on the metal surfaces as training data;
a presentation unit that presents a result information including an estimated grain size to a user; and
when the user changes the result information, the grain size estimation device attaches an identifying information to the changed result information that distinguishes the changed result information from the result information that is not changed.

12. A grain size estimation device comprising:
an acquisition unit that acquires a captured image of a surface segment of an object including metal;
an estimation unit that estimates a grain size of the surface segment of the object indicated in the acquired image, based on a predictive model generated by machine learning using images of metal surfaces and grain sizes on the metal surfaces as training data; and
wherein:
the acquisition unit acquires respective captured images of multiple surface segments on the object;
the estimation unit estimates respective grain size of each of the multiple surface segments on the object shown in the captured images; and
a result information including estimated grain sizes and a distribution of the grain sizes of each surface segment on the object is displayed on a display device.

* * * * *